US008571634B2

(12) United States Patent
Hubbard (10) Patent No.: US 8,571,634 B2
(45) Date of Patent: Oct. 29, 2013

(54) METHOD TO DIAGNOSE AND MEASURE VASCULAR DRAINAGE INSUFFICIENCY IN THE CENTRAL NERVOUS SYSTEM (76) Inventor: David R. Hubbard, Poway, CA (US)

( * ) Notice: Subject to any disclaimer, the term of this patent is extended or adjusted under 35 U.S.C. 154(b) by 0 days.

(21) Appl. No.: 13/497,950

(22) PCT Filed: Jul. 20, 2011

(86) PCT No.: PCT/US2011/044708
§ 371 (c)(1),
(2), (4) Date: Mar. 23, 2012

(87) PCT Pub. No.: WO2012/012553
PCT Pub. Date: Jan. 26, 2012

(65) Prior Publication Data
US 2012/0277572 A1    Nov. 1, 2012

Related U.S. Application Data (60) Provisional application No. 61/367,059, filed on Jul. 23, 2010.

(51) Int. Cl.
A61B 5/00    (2006.01)
(52) U.S. Cl.
USPC ........... 600/419; 600/410; 600/411; 600/407; 324/307; 324/308; 324/309
(58) Field of Classification Search
None
See application file for complete search history.

(56) References Cited

U.S. PATENT DOCUMENTS

2005/0085705 A1* 4/2005 Rao et al. .................. 600/345
2005/0107682 A1   5/2005 Rao et al.
2005/0110490 A1* 5/2005 Zhao et al. ................ 324/311
2006/0241374 A1  10/2006 George et al.
2007/0287904 A1* 12/2007 Li et al. ..................... 600/410
2009/0234236 A1   9/2009 Lomnes et al.

OTHER PUBLICATIONS

PZamboni, R Galeotti, E Manegatti, AM Malagoni, G Tacconi, S Dall'Ara, I Bartolomei, F Salvi. Chronic cerebrospinal venous insufficiency in patients with multiple sclerosis. J Neurol Neurosurg Psychiatry 2009; 80: 392-399.*
JA Detre, J Wang. Technical aspects and utility of fMRI using BOLD and ASL. Clinicla Neurophysiology 2002; 113: 621-634.*
P Sundstrom, A Wahlin, K Ambarki, R Birgander, A Eklund, J Malm. Venous and Cerebrospinal Fluid Flow in Multiple Sclerosis: A Case-Control Study. Annals of Neurol 2010; 255-259.*

(Continued)

Primary Examiner — Unsu Jung
Assistant Examiner — Amanda Laurirzen Moher
(74) Attorney, Agent, or Firm — Pattric J. Rawlins; Procopio, Cory, Hargreaves & Savitch LLP (57) ABSTRACT Neurodegenerative diseases, such as multiple sclerosis, may be caused or aggravated by insufficient venous draining from the central nervous system. Functional MRI measures the surge of blood flow into localized regions of cerebral cortex in response to activation of those regions by performing visual, auditory or executive tasks. These fMRI measurements are based on blood-oxygen-level dependence. The resulting fMRI/BOLD data is converted to hemodynamic response data and analyzed to determine any abnormality in the hemodynamic response data. Vascular drainage insufficiency is identified in the presence of abnormal hemodynamic response data. Abnormal hemodynamic response data can be determined by a negative trough in a graph of the HDR data or by the duration, depth, or area of the negative trough.

44 Claims, 5 Drawing Sheets

(56) References Cited

OTHER PUBLICATIONS

RJ Fox, E Beall, p. Bhattacharyya, J Chen, K Sakaie. Advanced MRI in Multiple Sclerosis: Current Status and Future Challenges. Neurol Clin. 2011; 29(2): 357-380.*

PCT/US2011/044708, PCT/ISA/210, Feb. 29, 2012, Korean Intellectual Property Office.
PCT/US2011/044708, PCT/ISA/237, Feb. 29, 2012, Korean Intellectual Property Office.

* cited by examiner

FIG. 1

FIG. 4 groups is presented in Table I.

Venous Undershoot in Multiple Sclerosis
David Hubbard MD

Pre Angioplasty

Post Angioplasty

*fMRI BOLD hemodynamic response shows clear improvement after angioplasty

METHOD TO DIAGNOSE AND MEASURE VASCULAR DRAINAGE INSUFFICIENCY IN THE CENTRAL NERVOUS SYSTEM

The present application is the U.S. National Stage of international patent application no. PCT/US2011/044708 filed on 20 Jul. 2011, which claims priority to U.S. provisional patent application No. 61/367,059 filed 23 Jul. 2010, each of which is incorporated herein by reference in its entirety.

BACKGROUND

1. Field of the Invention

The present invention is generally related to functional magnetic resonance imaging and the hemodynamic response to cognitive stimuli and is more specifically related to diagnosing and measuring vascular drainage insufficiency in the central nervous system using fMRI and BOLD.

2. Related Art

When the brain is active, it requires an increase in blood flow to the brain cells in the active region. The increase in blood flow typically occurs after a brief delay (e.g., 1-5 seconds) and usually peaks at around 4-5 seconds. After the peak, the increased blood flow washes out and typically exhibits a negative trough before returning to a normal baseline level. This process of increased blood flow and corresponding washout is referred to as a hemodynamic response ("HDR").

When the increased blood flow is delivered to the active region of the brain, the brain cells use the oxygen and glucose in the blood. Consequently, the deoxygenated blood remaining in the veins is paramagnetic and can be successfully imaged using magnetic resonance imaging. Imaging based on the magnetic contrast of deoxygenated blood is referred to as blood-oxygen-level dependence ("BOLD").

Functional magnetic resonance imaging ("fMRI") is used to capture complete scans of the brain during the HDR process, which typically takes about 15 seconds overall. The result of fMRI is a series of scans of the subject over time that show what region of the brain was active during the HDR. A single scan includes a full set of slices that cover the brain of the subject. Each slice is a separate image and collectively the slices comprise a three dimensional image of the brain of the subject. Typically, a scan is taken every 1-4 seconds. In this fashion, fMRI is used to identify the region of the brain that is active for a particular cognitive task.

SUMMARY

Conventional wisdom with respect to HDR is that the response proceeds nearly identically in all subjects, specifically that there is an increase in blood flow to a particular area responding to the increase in energy consumption by cells of that area and that the increased blood flow later washes out of the area and results in a slight trough, called the venous undershoot.

However the inventor has recognized that HDR is not identical in all subjects and more importantly that neurodegenerative diseases, such as multiple sclerosis ("MS"), may be caused or aggravated by insufficient venous draining from the central nervous system. Furthermore, the inventor has recognized that fMRI can be adapted to diagnose and measure vascular drainage insufficiency in the central nervous system.

Multiple sclerosis ("MS") is an inflammatory demyelinating disease and the causes of MS remain elusive and currently no cure exists for this condition. While it is widely considered to be of autoimmune nature, there is a renewed interest in the hypothesis that MS may be associated with impaired central nervous system venous drainage, for example, chronic cerebrospinal venous insufficiency ("CCSVI") caused by stenoses in large extracerebral veins. Such insufficiency may have direct consequences for both hemodynamics and function of cerebral parenchyma. Functional MRI based on BOLD contrast reflects both neuronal population responses and hemodynamics and the inventor has recognized that it can be used to assess changes in neuronal activity and hemodynamics due to MS.

In a group of MS patients, as compared to the control group, the magnitude of cognitive task-related BOLD signal modulation in gray matter was reduced in both the task-positive network and in the task-negative default mode network ("DMN") that is characteristically suppressed during task performance. Moreover, the HDR in some task-positive network areas exhibit increased post-stimulus undershoot, consistent with the hypothesis of impaired venous blood clearance. Remarkably, angioplastic treatment of jugular veins increased activity and reduced the BOLD undershoot in some task-positive areas and recovered activity in the DMN. Accordingly, HDR and BOLD can be used to identify and track improvements in MS symptomotology.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for systems and methods to diagnose vascular drainage insufficiency in the central nervous system. For example, one method as disclosed herein provides for converting fMRI/BOLD obtained from a subject in response to a particular cognitive task into HDR data and then analyzing the HDR data to determine an abnormal HDR and thereby identify a vascular drainage insufficiency in the central nervous system based on the abnormal HDR response. Additionally, a negative trough in a graph of the HDR data can be used to determine the abnormal HDR and the duration, depth or area of the negative trough can be used alone or in combination to determine the abnormal HDR.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

MS is one of the most prevalent neurodegenerative disease diagnosed in patients who are in the age range of 20 to 50 years. It is estimated that over 2 million people worldwide suffer form this condition. However, the etiology of this disease is presently unknown and there exists no cure for it. While it was proposed as early as in 1937 that MS might have a vascular etiology, presently the most popular theory regarding its causes is autoimmune theory and modern treatment of MS targets the immune system (e.g. by means of interferon-β). Recently a high incidence of CCSVI reported in MS patients generated much attention among MS researchers and patients alike because CCSVI can be treated using a relatively simple procedure, an angioplasty treatment targeting stenoses primarily in large extracerebral veins (such as jugular and azygos veins). Advantageously, establishing a causal relationship between MS and CSSVI may have dramatic consequences for understanding MS etiology and possibly help find a cure for it.

One of the hallmarks of MS is lesions containing demyelinated axons and clustering around venules and veins of CNS white matter. White matter ("WM") demyelination that results in disconnection of axons interconnecting cortical (and subcortical) regions is thought to be the neural basis of cognitive impairments in MS.

Among most common cognitive impairments associated with MS are motor dysfunction, mood disorders, memory and attention deficits, with information processing speed and memory disorders dominating in relapsing-remitting MS ("rrMS"). Previous PET brain imaging studies addressing functional correlates of cognitive impairment in MS found widespread gray and white matter reduction in cerebral metabolic rate of glucose and oxygen ("CMRglu, CMRO2") that correlated with both the WM lesion load and impairment in executive control, attention processes and long-term memory.

Subsequent MRI studies addressing the relationship between WM lesion load and fMRI responses during cognitive and motor tasks, found correlations between the two measures in both the motor and episodic memory system. Interestingly, BOLD activation associated with motor tasks differed in both magnitude and distribution in MS patients as compared to controls, which was interpreted as evidence for compensatory reorganization of motor task-related cortical networks. Increased BOLD activation in MS patients as compared to controls was also observed in prefrontal cortex during attention-demanding tasks, and episodic memory retrieval. However, in light of earlier PET results that found generalized cerebral metabolic rate reduction in MS patients and the fact that BOLD signal is a function of both cerebral metabolism rate and blood flow, this enhancement in BOLD responses needs to be interpreted carefully, as it may be an outcome of, for example, reduced baseline neuronal activity.

Default mode network, thought to mediate intrinsic states such as self-referential processes, moral judgment and episodic future planning is also affected in MS patients. DMN is suppressed during cognitive task performance or other externally-oriented activity, and the degree of its suppression correlates with cognitive performance. The functional connectivity among areas belonging to DMN (e.g., ventral medial prefrontal cortex, posterior cingulate cortex, inferior parietal lobule, hippocampal formation, anterior part of the inferior temporal sulcus) is preserved during resting state. In patients with both primary progressive MS ("ppMS") and secondary progressive MS ("spMS") DMN activity as measured by resting state correlations is substantially diminished in all cortical areas of DMN, with anterior cingulate cortex ("ACC") affected more in spMS. The reduction in DMN activity correlated with measures of memory performance, consistent with recent reports that DMN is involved in memory encoding and retrieval. In addition, reduced activity in DMN of MS patients also correlated with diffusion MRI measures of WM damage, such as mean diffusivity and fractional anisotropy, thus further supporting the notion that functional impairments in MS are an outcome of the structural damage to WM.

Recently, the hypothesis that MS may be associated with impaired CNS venous drainage was revisited and revealed a high incidence of CCSVI in MS patients. This finding is consistent with long acknowledged deficiency of cerebral blood flow ("CBF") in MS, and raises a hypothesis that at least some of the MS symptoms, including cognitive impairments and reduced neuronal responses as measured by BOLD fMRI, are a direct consequence of impaired cerebral venous blood clearance.

The inventor addressed this hypothesis by measuring BOLD responses in MS patients performing a cognitive task before and after an angioplastic treatment of CCSVI. It was found that BOLD responses in task-positive cortical and subcortical regions as well as BOLD response suppression in DMN (task-negative regions) were much reduced in MS patients as compared to controls. Furthermore, the shape of HDR functions differed from controls in some cortical areas of MS patients, the most prominent feature being an increased after-stimulus undershoot, which is consistent with compromised clearance of venous blood from gray matter venules.

Most importantly, BOLD responses after the angioplastic procedure increased in some task-positive cortical areas, and task-related suppression of DMN recovered to levels comparable to that of the control group. Moreover, the procedure resulted in a trend towards a smaller negative trough area of the after-stimulus undershoot. These changes in BOLD response magnitude and HDR shape brought about by angioplasty are in the direction towards the values observed in the control group. The most prominent among those changes was the recovery of the DMN activity after the procedure. The exciting conclusion is that the angioplastic intervention in MS patients suffering from CCSVI normalizes cortical BOLD responses in these patients and is likely to alleviate MS symptoms. Although the angioplasty effect on BOLD responses may have both neuronal and vascular components that the BOLD signal cannot disentangle, simultaneous BOLD and CBF measurements by means of arterial spin labeling ("ASL") will disentangle these contributions.

Certain aspects of the invention will now be described in the context of an example test that was performed in which the functional and structural MRI scans from twenty MS/CCSVI patients (14 females) were analyzed as a part of diagnostic evaluation for the angioplasty. Fifteen normal control subjects (9 females) were also scanned using identical protocols.

MS patients were scanned before an angioplastic procedure and one to two days after the procedure. Thirteen of those subjects had a confirmed relapsing-remitting type ("rrMS") and two were diagnosed with primary progressive MS ("ppMS").

Figure 1:
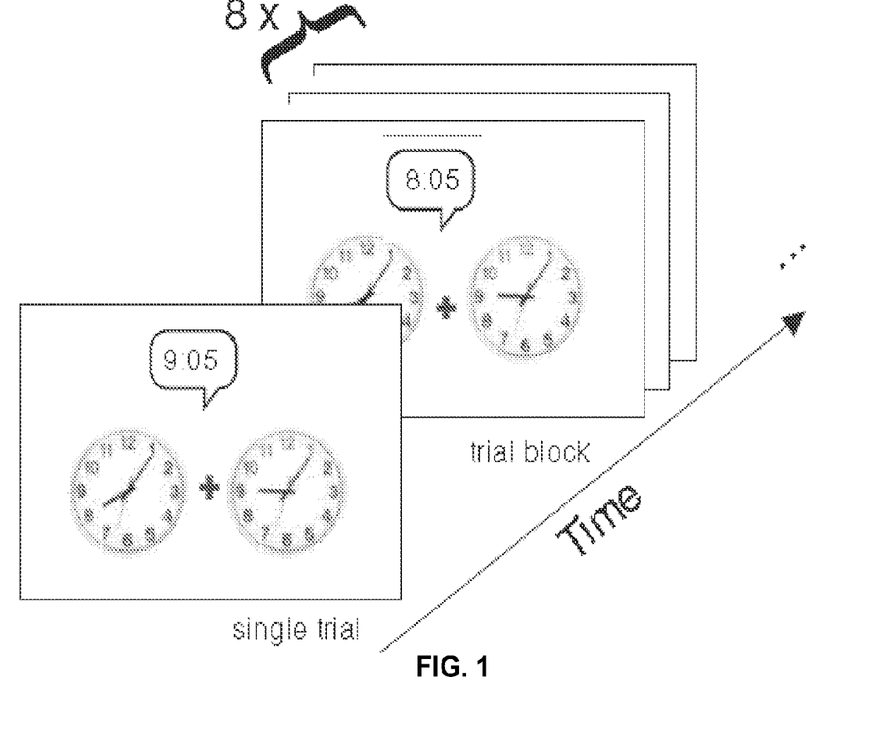
FIG. 1 is a block diagram illustrating an example of a task called Tell Time according to an embodiment of the present invention.

FIG. 1 is a block diagram illustrating an example Tell Time task according to an embodiment of the present invention. In the Tell Time task, subjects listened to spoken time statements (hours and minutes) and simultaneously viewed two clock faces presented on both sides of the fixation cross. The subject's task is to indicate the clock that showed the time that differed from the spoken one. A single three second task trial is followed by a thirty-eight second fixation interval followed by a block of eight trials and a sixty-one second fixation interval. Alternative tasks or protocols can also be administered to the patient, for example finger tapping tasks and language tasks. Additional tasks or protocols or other alternative tasks or protocols may also be administered to the patient as will be understood by those skilled in the art.

The cognitive task is designed to activate a maximum number of cortical and subcortical regions while still being intuitive to an untrained person. While in the scanner, subjects hear a spoken time of day via MR-compatible headphones (e.g., Avotec Inc., Sturat, Fla.) and simultaneously see a display screen with a fixation cross presented thereon with two clock faces, one on each side of the display screen as shown in FIG. 1. The Tell Time task is presented during each trial via a projector (e.g., 5200 lumens, NEC NP4000, Tokyo, Japan) using a presentation program (e.g., such as that provided by Neurobehavioral Systems, Inc., Albany, Calif.). In one embodiment, the distance from the subject's eyes to the screen is about 36 inches and each clock face subtended 6.4 degrees of visual angle.

In the Tell Time task, one of the clocks shows a time that is the same as the spoken time, while the other clock shows a time that is different from the spoken time. The subject is instructed to press a button on an MRI-compatible response box (e.g., FORP, Current Designs, Philadelphia, Pa.) indicating which side of the fixation cross has the clock showing the time is different from the spoken time. In one embodiment, each trial is repeated seven times as follows: first, a single task is presented followed by a thirty-eight second fixation interval, then a block of eight tasks is presented followed by sixty one seconds of fixation. The first trial is presented after forty-four seconds (22 TRs) from the beginning of the EPI scan for the purpose of establishing a baseline signal. This temporal pattern is aimed at revealing hemodynamic responses (HDRs) associated with a single vs. blocked tasks.

During the example test mentioned above, MRI scans of control subjects and MS patients were acquired using a Siemens Trio 3T system. MS patients were scanned before and after undergoing the angioplastic procedure. Structural scans at the resolution of 1×1×1 mm voxels were acquired using MP-RAGE protocol (TR/TE/TI=1900/2.26/900 ms, flip angle=9 deg). Functional T2*-weighted images were acquired using gradient echo EPI sequence with parameters TR/TE=2000/25 ms, flip angle=90 degrees, 36 slices of thickness=3 mm, in-plane resolution: 3.75×3.75 mm2, spacing between slices=4 mm. The number of repetitions was 463 resulting in scan duration of 15.37 minutes.

Additionally, as part of the example test MRI image pre-processing and processing steps were performed with a custom-developed analysis toolbox for Matlab (MathWorks, Natic, Mass.) with integrated calls to a subset of functions from the AFNI (Cox, 1996), FSL (Smith et al., 2004) and mrVista (mrVista, 2011) software packages. Structural scans were processed by computationally removing skull and aligning to the Talairach-Tourneaux space (TT-space). Functional scans were smoothed with a five mm smoothing kernel, resampled at four mm resolution, head motion was corrected by aligning volumes at each time point to a reference volume and the resulting volumes were stripped of skull, aligned to structural scans and mapped to the TT-space. A reference function, created by convolving task occurrence times with a standard gamma distribution function, was then used for calculation of first-level individual t-maps by means of the generalized least squares fitting procedure as implemented in 3dREMLfit. Head motion parameters were projected out from fMRI time series at this step. At the second step, group statistical maps were calculated using a mixed-effects procedure implemented in 3dMEMA. Mixed-effects t-maps were generated for each experimental group (controls, pre-angio and post-angio) as well as for group differences (control vs. pre-angio and pre- vs. post-angio). Group t-maps for the control group were thresholded at $p<0.05$ ($|t|>2.1$) and multiple comparison-corrected significantly active voxel clusters were then determined using permutation analysis ($p<0.01$).

For evaluation of the extent of active regions in terms of the number of active voxels and time course of hemodynamic responses masks were first created for regions of interest ("ROI") in the following way: active voxel clusters determined in pooled group analysis of control subjects and MS patients, as described above, were intersected with anatomy based regions derived from the Talairach-Tourneaux atlas thus resulting in anatomically constrained cortical and subcortical ROI masks for both task-positive areas (positive response magnitudes) and task-negative areas that coincided with the DMN negative response magnitudes. The task-positive ROIs and corresponding Brodmann's areas (for cortical regions) are listed in Table 1.

TABLE I

Voxel counts in anatomical regions with task-positive or task-negative active voxel clusters.

| Anatomical Region | Brodman's areas | Control group Voxel # ± stderr | Pre-angio group Voxel # ± stderr | Post-angio group Voxel # ± stderr |
|---|---|---|---|---|
| Task-positive areas | | | | |
| All task-positive areas | n/a | *27261 ± 5636 | **15738 ± 7807 | 22479 ± 6629 |
| Occipital poles | 17, 18, 19 | 5042 ± 727 | 4370 ± 1792 | 4043 ± 1574 |
| Fusiform, Parahippocampal gyri (FFG, PHG) | 20, 36, 37 | 1278 ± 301 | 1180 ± 565 | 1237 ± 351 |
| Superior temporal cortex (STC) | 21, 22, 41 | 3601 ± 700 | 3993 ± 1543 | 3354 ± 862 |
| Superior and inferior parietal lobules (SPL, IPL), precuneus | 7, 40 | 2757 ± 706 | **1559 ± 858 | 2230 ± 728 |

TABLE I-continued

Voxel counts in anatomical regions with task-positive or task-negative active voxel clusters.

| Anatomical Region | Brodman's areas | Control group Voxel # ± stderr | Pre-angio group Voxel # ± stderr | Post-angio group Voxel # ± stderr |
|---|---|---|---|---|
| Precentral gyrus (PCG) | 6, 4 | 2757 ± 706 | 1559 ± 858 | 2230 ± 728 |
| Cingulate gyrus (CG) | 24, 32 | 307 ± 60 | 378 ± 165 | 414 ± 112 |
| Dorso-lateral prefrontal cortex (DLPFC) | 9, 45, 46 | 907 ± 212 | 1418 ± 635 | 1335 ± 358 |
| Thalamus | n/a | 1356 ± 179 | 819 ± 403 | 765 ± 414 |
| Basal ganglia (BG) | n/a | 467 ± 144 | 561 ± 328 | 414 ± 213 |
| Cerebellum | n/a | 5059 ± 1090 | 3331 ± 1848 | 3311 ± 990 |
| Task-negative areas | | | | |
| All task-negative areas (DMN) | n/a | 1215 ± 361 | **573 ± 260 | ***1038 ± 231 |
| Anterior cingulate cortex (ACC), medial frontal gyrus (MFG) | 24, 32, 10 | 1087 ± 336 | 407 ± 225 | ***724 ± 164 |
| Superior frontal gyrus (SFG) | 8, 9 | 62 ± 16 | 134 ± 92 | 111 ± 56 |
| Posterior cingulate cortex (PCC), precuneus | 23, 30, 31 | 20 ± 10 | 28 ± 14 | 31 ± 11 |
| Middle temporal gyrus (MTG), angular gyrus (AG) | 7, 18, 39 | 120 ± 41 | **12 ± 4 | 100 ± 47 |
| Temporal poles (TP), anterior superior and inferior temporal gyrus (STG, ITG) | 21, 38 | 37 ± 14 | 95 ± 63 | 23 ± 14 |

*significant effect across the three groups ($p < 0.05$, Kruskal-Wallis test, nonparametric ANOVA).
**mean of pre-angio group significantly less than that of the control group ($p < 0.05$, Wilcoxon test)
***mean of pre-angio group significantly less than that of the post-angio group ($p < 0.05$, Wilcoxon test)

This procedure assured minimum circularity in fMRI data analysis. For quantification of task-related effects in different ROIs, the number of significantly activated ($p < 0.01$, corrected) or suppressed ($p < 0.05$, corrected) voxels were counted within each ROI of each subject and group mean and standard error was calculated.

Next, for estimation of hemodynamic response function shapes, these ROIs were used to constrain significantly active voxels for extraction of time series of individual scans. The specificity of BOLD response increases when weakly responding or low signal to noise ratio ("SNR") voxels are eliminated from analysis by increasing the t-map threshold. The voxels with maximum response magnitude contained large draining veins. For task-positive and task-negative ROIs different t-values were used that yielded comparable BOLD response specificity. Hence, for task-positive voxels $t > 6$ was used and for the task-negative voxels $t < -4$ was used. These values resulted in consistent detection of activation in both task-positive and task-negative areas of MS patients. The time series data were smoothed in the temporal domain (e.g., Gaussian kernel of two second standard deviation) and averaged both voxel-wise and block-wise and the peak value was normalized to one (1) for each subject before calculating group averaged HDRs and standard errors of the mean. The significance of the post-stimulus undershoot was then evaluated (following the response to the block of eight trials) by running t-tests comparing undershoot trough magnitudes estimated as means within time windows (see the shaded rightmost regions in FIG. 3). Undershoot magnitude outliers were then eliminated before the data was submitted for statistical tests.

Figure 2:
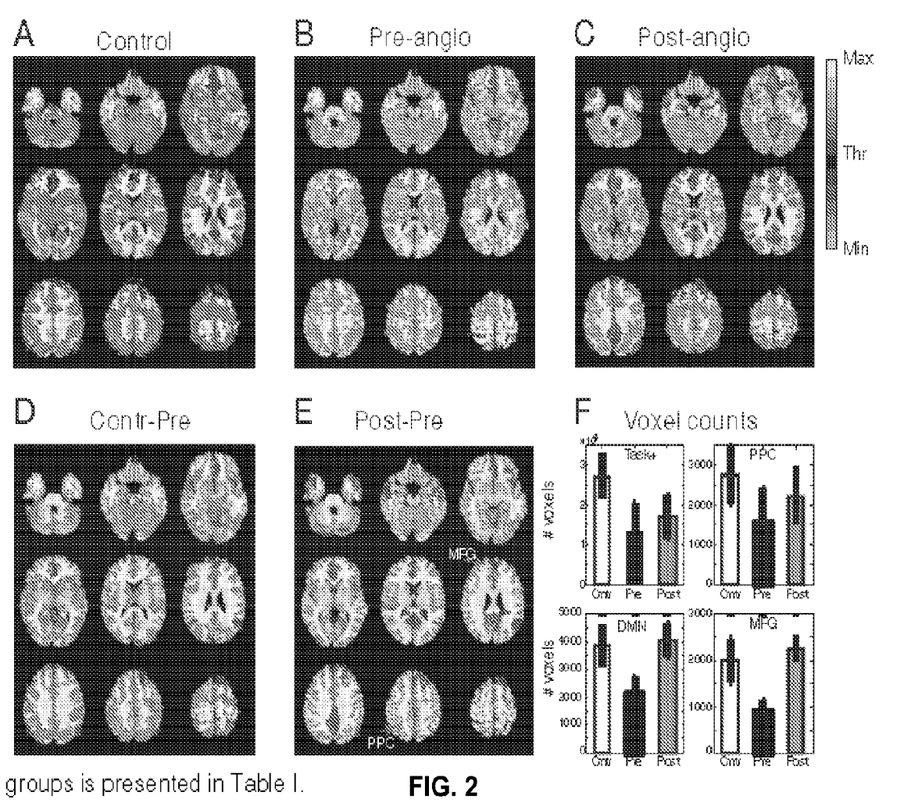
FIG. 2 is a statistical parametrical map diagram illustrating example fMRI data according to an embodiment of the present invention.

FIG. 2 is a statistical parametrical map diagram illustrating example fMRI data according to an embodiment of the present invention. Statistical parametrical maps (t-values, threshold Thr>2.1) are shown in FIG. 2 for:

(A) the control group (Max=15, Min=−11);
(B) MS patient pre-angio group (Min=−6, Max=7);
(C) MS patient post-angio group (Min=−9, Max=8);
(D) control—pre-angio (Min=−7, Max=9);
(E) paired t-test map for post-angio—pre-angio group differences (Min=−8, Max=4; note the color bar range differences); and
(F) Voxel counts in control (white bars), pre-angio (black) and post-angio (grey) groups for task-positive (Task+), task-negative (DMN), posterior parietal cortex (PPC) and medial frontal gyrus (MFG) ROIs.

In the example test, both MS patient and control groups performed the Tell Time task with very few errors (>95% correct rate) and the performance levels did not differ between control and patient groups. In the control group the task evoked activation in an extensive set of brain areas (task-positive network), including visual (occipital, fusiform and parahippocampal cortex), auditory (posterior superior temporal gyrus and angular gyrus), association and executive regions (parietal, temporal and frontal lobes) as well as subcortical structures including basal ganglia, thalamus and cerebellum (shown by the red/orange voxels in FIG. 2A and Table 1). Cortical areas suppressed during the task performance (task-negative network) included medial prefrontal, anterior and posterior cingulate cortex and cuneus (shown by the blue voxels in FIG. 2A and Table 1) and thus coincided with the default mode network.

In the MS patient group, task performance evoked task-positive activation that was substantially reduced as compared to the control group. Moreover, suppression in cortical areas of the DMN was nearly absent (FIGS. 2B and 2D). However, after the angioplastic procedure activation in the task-positive network increased in some areas (e.g., in PPC and occipital poles). Most remarkably, suppression in the DMN areas was completely recovered (FIGS. 2C and 2E).

FIG. 2F plots voxel counts for task-positive network (top row bar plots) and DMN (bottom row bar plots). While the active voxel count is much reduced in pre-angio MS patients, the mean post-angio voxel count in task-positive network shows a tendency to increase and in DMN the number of significantly suppressed voxels is nearly identical to that of the control group. A full list of active voxel counts in each ROI for all three groups is presented in Table 1.

Figure 3:
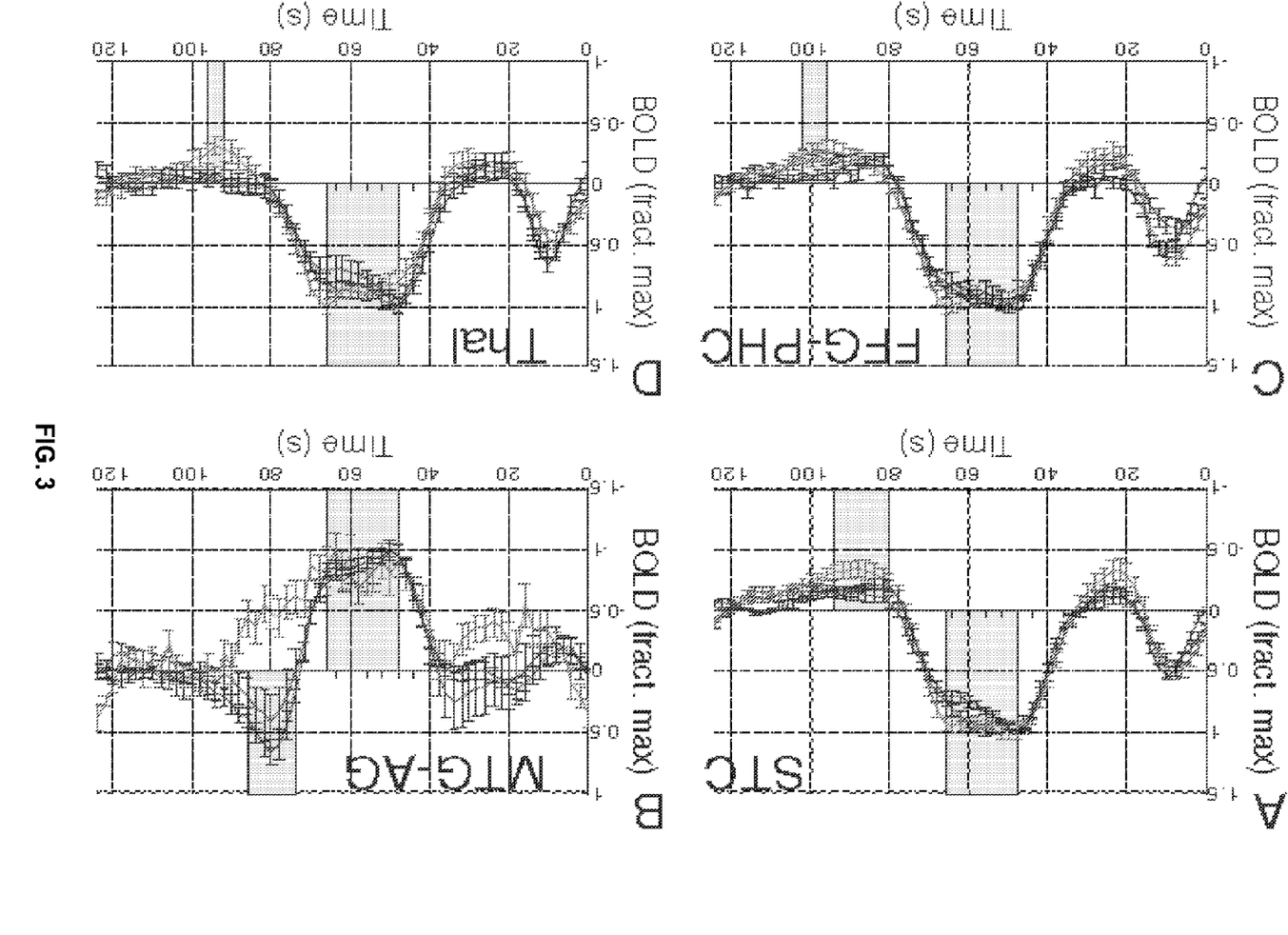
FIG. 3 is a graph diagram illustrating example HDR data according to an embodiment of the present invention.

FIG. 3 is a graph diagram illustrating example HDR data according to an embodiment of the present invention. The HDR is calculated from fMRI data obtained from scans of the patient during and after performance of the Tell Time task. FIG. 3 illustrates group-averaged normalized HDR functions for control (black), pre-angio (red) and post-angio (blue) groups.

(A) HDRs for the task-positive ROI in the superior temporal cortex (STC) ROI (control vs. pre-angio t-test, $p<0.05$, one-sided; pre-angio vs. post-angio t-test, $p<0.05$, one sided).

(B) HDRs for task-negative (DMN) ROI in the MTG-AG. Note that in the top row panels (A,B) undershoots of pre-angio group HDRs differ statistically significantly from both control and post angio groups. Remarkably, HDRs of control and post-angio patient groups are nearly identical.

(C) HDRs for task-positive ROI in FFG-PHC. In this case both pre- and post-agio HDRs are nearly identical and there is a trend towards prolonged HDR undershoot as compared to the control group HDR.

(D) HDRs for the thalamic ROI (pre- vs. post-angio t-test, $p=0.07$). Error bars are standard error of the mean. Short vertical tics on the horizontal zero-line represent times of task onset. Grey regions indicate time intervals for HDR normalization (left) and estimation of undershoot magnitude (right).

HDRs from four ROIs that exhibited substantial time course differences across the three groups are shown in FIG. 3. Hemodynamic responses in a minority of the fifteen ROIs (Table 1) of MS patients before angioplasty differed from those of controls, with the most salient and consistent difference occurring in the magnitude (e.g., FIG. 3A) or the duration (FIGS. 3C and 3D) of the post-stimulus undershoot.

Importantly, HDRs in the task-positive ROIs of the post-angio patient group had a tendency to match the time course close to that observed in control subjects (FIGS. 3A and 3D). But see also FIG. 3C where the duration of undershoots of pre- and post-angio HDRs are identical and differ from that of the control group. HDRs of task-negative ROIs also had a tendency to assume time courses similar to those of the control group (FIG. 3B).

In view of the test example data, the observed differences in BOLD activation patterns and time courses in MS vs. control groups suggests a substantial reorganization in neurovascular activity in cortical and subcortical grey matter in MS patients, consistent with previous studies that found generalized reduction in cerebral metabolic rate and cerebral perfusion. These previous studies also reported moderate correlations between WM lesion load and reduction in metabolism and perfusion. Furthermore, the total lesional area was found to be larger in MS patients with impaired cognition as compared to those with unimpaired. Such results have been interpreted as evidence that cognitive impairments and associated reduction in cerebral metabolism/perfusion are an outcome of the structural damage to WM including lesions and normally appearing white matter ("NAWM").

However, in the test example, the recovery after angioplasty of BOLD activity in several cortical and subcortical regions, most dramatically in cortical areas of DMN, occurred within one to two days, which is insufficient for WM repair through remyelination. Altered HDR time courses in certain grey matter ("GM") ROIs of MS patients and HDR normalization after venous angioplasty provides evidence that obstruction of flow and/or refluxes in extracranial veins affects the hemodynamics in the microvasculature of cerebral parenchyma. This suggests that alteration in BOLD responses in MS patients can be at least partially attributed to factors associated with CCSVI and not to factors associated with WM demyelination or related structural degradation.

Several previous fMRI studies addressed brain activation during cognitive and motor tasks and reported increased BOLD responses in MS patients. These studies employed tasks that required substantial cognitive or motor effort on the part of subjects. It is likely that in these studies patients with cognitive or motor impairments found those tasks more demanding than controls, as task difficulty control was not performed in the prior studies. Levels of task difficulty are known to correlate with activity in fronto-parietal cortical network involved in executive function and memory/attention tasks. Thus, it is likely that stronger activation in MS patients was evoked due to the compensatory effort required by MS patients. Moreover, increased BOLD responses can also occur as a result of decreased baseline CBF. Thus, decreased CBF in MS patients likely also accentuated increases in BOLD responses.

The Tell Time task, by contrast, is a variation of a familiar task (time-telling done everyday), and was performed with a very low error rate by both control and MS subjects.

DMN suppression recovery by angioplasty has important implications for cognition in MS. Impairments in DMN activity are common in psychiatric and neurological pathology: DMN activity deficits have been reported in clinical depression patients, ADHD patients, schizophrenia and Alzheimer's disease. While DMN is primarily considered to be involved in self-referential, or internal information processing, recent studies implicate DMN in episodic memory function: Recent correlation analysis of the resting state fMRI time courses have revealed strong functional connectivity between hippocampus and DMN areas and showed that parietal regions of DMN (AG, MTG, TPJ) are involved in episodic memory recall.

Episodic memory impairment is among the most common cognitive impairments in MS. Previous studies of the resting state correlations in the DMN network areas found a reduced activation in MS, which is consistent with the text example results. Thus, recovery of DMN modulation (task-related suppression) after angioplastic procedure improves episodic memory in MS patients and alleviates other cognitive disorders associated with impairment of DMN function.

BOLD signal values depend on deoxyhemoglobin concentration in a voxel and thus BOLD responses are a complex function of baseline values of CBF, CBV and CMRO2 and also of changes of these values due to neuronal activity. For example, on one hand, an increase in CBF results in increased BOLD signal. On the other hand an increase in CMRO2 results in a decrease in BOLD signal. Thus, in light of previously reported reductions in both CBF and CMR in MS patients, the BOLD signal alone cannot be used for definitive determination of the mechanisms of altered BOLD responses in MS. Furthermore, BOLD response reduction in task-positive areas reflects not only a decrease in neuronal population responses, but also changes in neurovascular coupling (e.g., reduction in CBF response, increase in CMR response relative to reduced baseline CMR, etc.). Therefore, disentangling vascular and metabolic contributions to the BOLD signal can be accomplished using techniques such as arterial spin labeling ("ASL").

In some areas of MS patients, enhanced HDR undershoot was observed in the text example. The enhanced HDR undershoot returned to the shape identical to that of the control group after the angioplasty. The Balloon Model assumed herein, postulates that the volume of the venous blood in the venules increases transiently in response to increased CBF, and returns back to baseline with a delay thus resulting in post-stimulus undershoot. According to this model, the BOLD post-stimulus undershoot reflects dynamics of clearance of venous blood, therefore, extended undershoot in MS patients according to this model corresponds to prolonged clearance of venous blood from the capillary bed.

Figure 4:
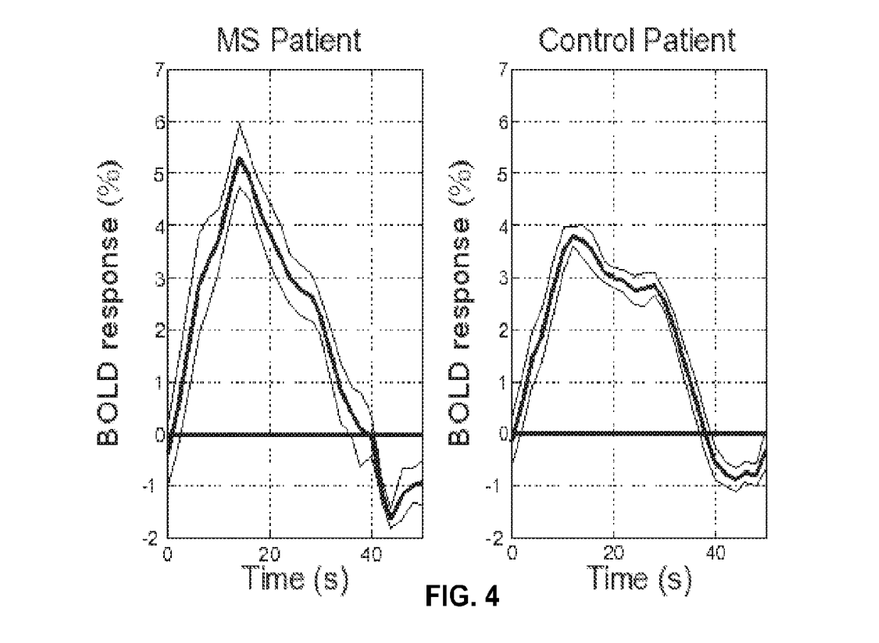
FIG. 4 is a graph diagram illustrating example fMRI data graph of BOLD over time and showing the hemodynamic response in a multiple sclerosis patient and a control patient according to an embodiment of the present invention.

FIG. 4 is a graph diagram illustrating example fMRI data graph of BOLD over time and showing the hemodynamic response in a multiple sclerosis patient and a control patient according to an embodiment of the present invention. In the illustrated embodiment, the HDR graph for an MS subject is contrasted with the HDR graph for a control subject. As shown, the peak for the MS subject is higher than the peak for the control subject. Additionally, the negative trough for the MS subject is lower than the negative trough for the control subject.

Figure 5:
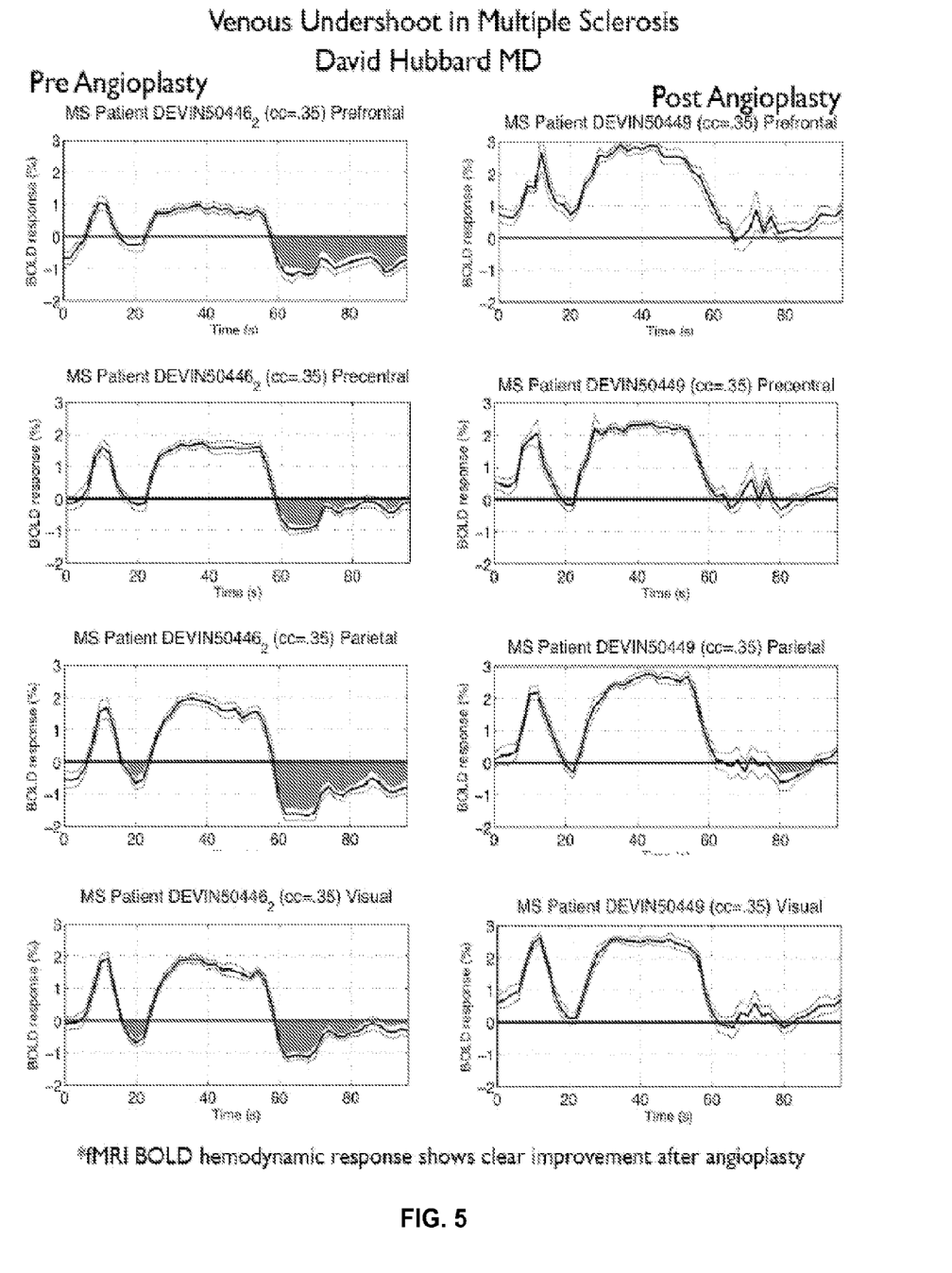
FIG. 5 is a graph diagram illustrating example fMRI data graph of BOLD over time and showing the hemodynamic response in a multiple sclerosis patient prior to angioplasty and after angioplasty according to an embodiment of the present invention.

FIG. 5 is a graph diagram illustrating example fMRI data graph of BOLD over time and showing the hemodynamic response in a multiple sclerosis patient prior to angioplasty and after angioplasty according to an embodiment of the present invention. In the illustrated embodiment, the pre-angioplasty graphs represent four different regions of the subject's brain, namely prefrontal, precentral, parietal and visual. In the illustrated embodiment, each region demonstrates a similar HDR determined based on the fMRI BOLD measurements. Advantageously, examination and analysis of the HDR from different regions of the brain may be suggestive of the location of vascular drainage insufficiency.

In the illustrated embodiment, each graph represents a single task (the first peak) followed by a block of tasks (second, prolonged peak). In the pre-angioplasty graphs, there is a deep trough after the single task and a deep and prolonged trough after the block task. In the post angioplasty graphs, the negative troughs during washout are significantly improved.

In one embodiment, a specifically designed cognitive task sequence is used to elicit the desired fMRI BOLD data that can be analyzed to generate the HDR graph. For example, the cognitive task sequence includes a single task followed by a block task (multiple tasks). These tasks advantageously may involve executive and other brain functions as desired.

Figure 6:
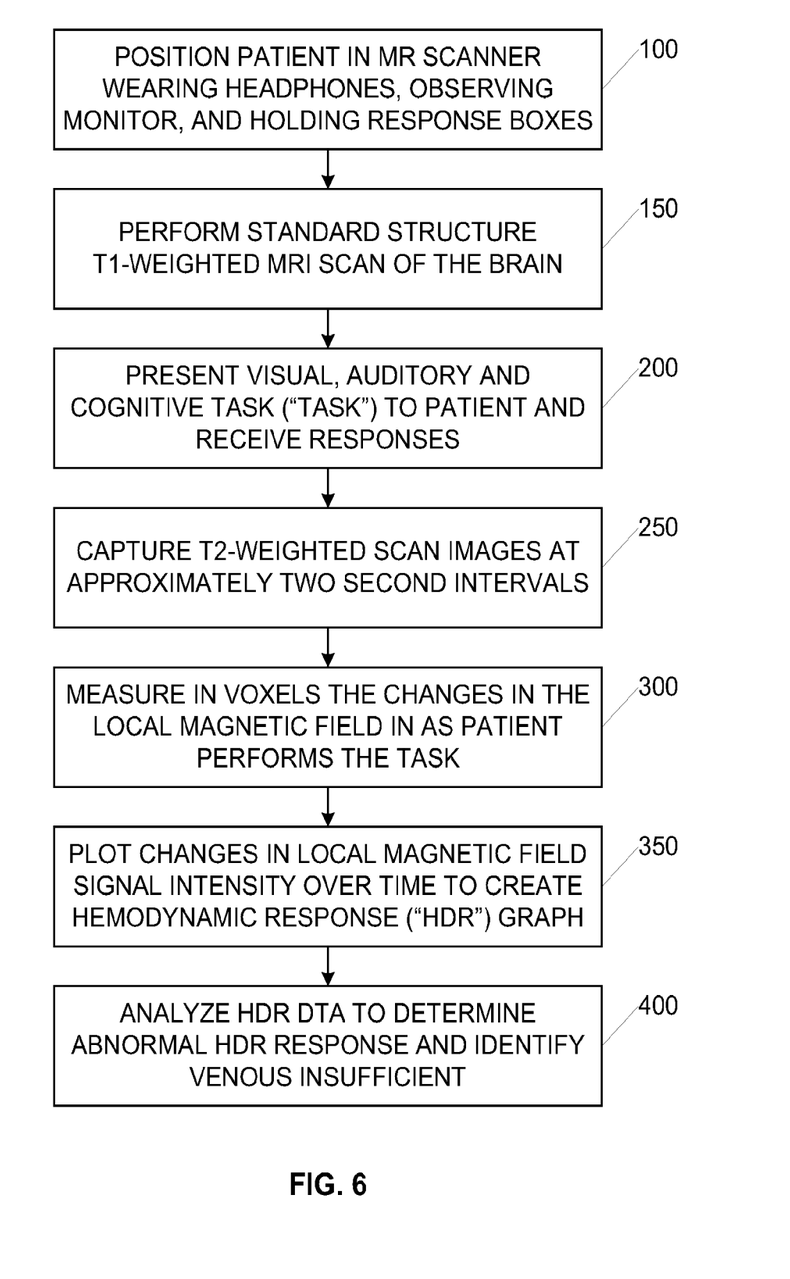
FIG. 6 is a flow diagram illustrating an example fMRI process adapted to diagnose vascular drainage insufficiency in the cerebral cortex according to an embodiment of the present invention.

FIG. 6 is a flow diagram illustrating an example fMRI process adapted to diagnose vascular drainage insufficiency in the central nervous system according to an embodiment of the present invention. In a broad sense, the illustrated embodiment of the present invention analyzes fMRI BOLD data and generates HDR data to measure and diagnose vascular drainage insufficiency in the central nervous system. For example, the amount and duration of venous delay in multiple cerebral cortex regions in response to a cognitive task are measured and analyzed to diagnose vascular drainage insufficiency in the central nervous system.

Initially, in step 100 of the illustrated embodiment, a subject (e.g., MS patient or control subject) is placed in an MR scanner having means to deliver aural and visual information to the subject. For example, the subject may be wearing headphones and positioned to observe a display monitor. In this way, the subject can be aurally and visually engaged during scanning. The subject is also holding response boxes, one in each hand, so the subject can interact with aural and visual stimulation.

Next, in step 150 a standard structure T1-weighted MRI scan of the brain is taken to establish a baseline for the individual subject. In alternative embodiments, the structural MR scan may be performed before or after the functional MR scan.

Then in step 200 a visual, auditory and cognitive task is presented to the subject through the headphones and the display monitor. For example, the Tell Time task is presented to the subject. Responses from the subject are received via the response boxes that are held in the subject's hands. For example, the subject holds a first response box in the left hand and holds a second response box in the right hand.

Next in step 250 a T2-weighted scan of the brain is performed to capture images at approximately two second intervals. The scan images reflect the HDR in multiple brain regions and the resulting images include voxels (volumes of brain tissue, typically in the 1-9 mm cubed range). In step 300, the changes in the local magnetic field are measured in voxels as the subject performs the task. These changes in the local magnetic field signal intensity are then plotted over time to create an HDR graph as shown in step 350. For example, the positive and negative amplitudes and time course of the HDR is calculated based on the fMRI BOLD data that is captured by the MR scanner.

Finally, in step 400 the HDR graph is analyzed to determine if the HDR response is abnormal and vascular drainage insufficiency in the central nervous system can be identified based on the abnormal HDR response. This can be achieved by comparing the HDR data to a database of normal values to identify abnormal HDR. A pattern significantly different from normal may indicate pathology in the flow of blood within the cerebral cortex and a prolonged or more negative trough may indicate a vascular drainage insufficiency in the central nervous system. Components of the central nervous system that can be diagnosed include the cerebral cortex, sub-cortical white matter, thalamus, basal ganglia, brainstem, and the spinal cord.

Additionally, when the HDR data is analyzed, for example as a graph, an abnormal HDR response can be identified by a negative trough in the HDR data. In addition, abnormal HDR can be identified by the duration of the negative trough, the depth of the negative trough, or the area of the negative trough in the HDR data.

In the illustrated embodiment, the analysis of the HDR is automated and incorporated into a computer that controls the scanner. Alternatively, the HDR analysis can be incorporated into a separate computer that has access to the fMRI BOLD data so that the HDR data can be generated and analyzed and compared.

As will be understood by those skilled in the art, structural and functional MR scanning is performed in the typical manner. The resulting images can be stored in accordance with the digital imaging and communications in medicine ("DICOM") standard and can also be exported from the scanner to a computer for the analysis. As previously described, the analysis may also be performed by the MR scanner device. As will be understood, open-source, propriety or ad hoc software may be employed to facilitate the image analysis.

In the example embodiment, a number of brain regions may be selected for analysis and the HDR calculated for each region. Patterns of HDR can be analyzed for individual regions or in combination and compared to the database in the same single or collective fashion to identify abnormal patterns. Advantageously, evidence of prolonged or deep venous undershoot are indicative of cerebral venous insufficiency.

In one embodiment, the system for presenting visual, auditory and executive tasks to a patient or research subject may be packaged into a combination of hardware and software, for example hardware and software that are incorporated into an MR apparatus. The software for analyzing the HDR data may also be incorporated into an MRI scanner device or it may be resident on a separate computer device that has access to the fMRI BOLD data that is generated by the MR scanner.

Figure 7:
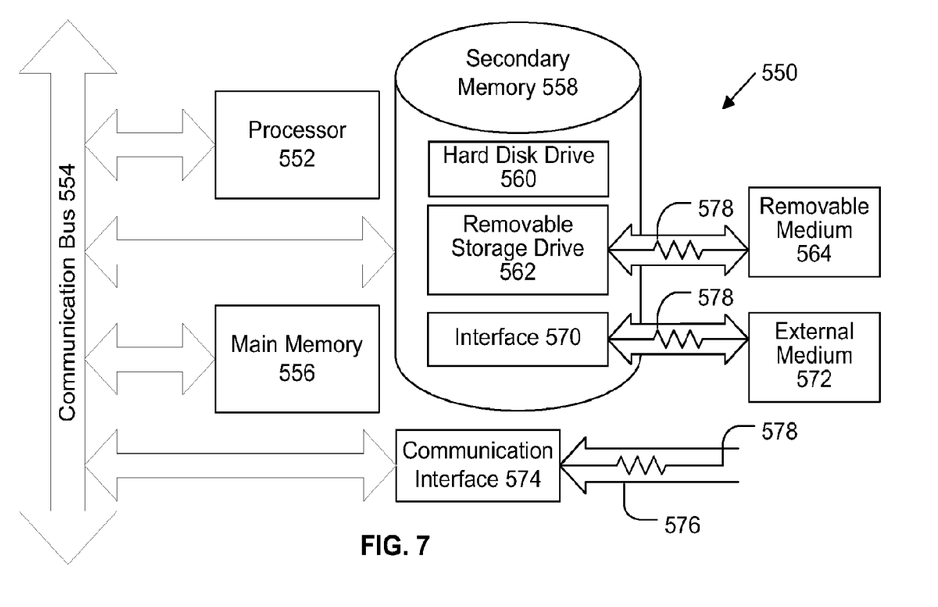
FIG. 7 is a block diagram illustrating an example computer system that may be used in connection with various embodiments described herein.

FIG. 7 is a block diagram illustrating an example computer system 550 that may be used in connection with various embodiments described herein. For example, the computer system 550 may be used in conjunction with a functional magnetic resonance imaging machine or an fMRI analysis station. However, other computer systems and/or architectures may be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any non-transitory computer readable storage media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These non-transitory computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A functional magnetic resonance scanner apparatus comprising at least one processor communicatively coupled with at least one non-transitory computer readable medium, wherein the processor is programmed to:
    obtain functional magnetic resonance imaging ("fMRI") data based on blood oxygen level dependence ("BOLD");
    convert the fMRI/BOLD data to hemodynamic response ("HDR") data comprising a graph of the BOLD over time;
    analyze the HDR data to determine an abnormal HDR response by identifying a negative trough in the HDR data;
    identify a vascular drainage insufficiency in the central nervous system based on said abnormal HDR response.

2. The apparatus of claim 1, wherein an abnormal HDR response is identified by the duration of the negative trough in the HDR data.

3. The apparatus of claim 1, wherein an abnormal HDR response is identified by the depth of the negative trough in the HDR data.

4. The apparatus of claim 1, wherein an abnormal HDR response is identified by the area of the negative trough in the HDR data.

5. The apparatus of claim 1, wherein the HDR data is related to the cerebral cortex.

6. The apparatus of claim 1, wherein the HDR data is related to the sub-cortical white matter.

7. The apparatus of claim 1, wherein the HDR data is related to the thalamus.

8. The apparatus of claim 1, wherein the HDR data is related to the basal ganglia.

9. The apparatus of claim 1, wherein the HDR data is related to the brainstem.

10. The apparatus of claim 1, wherein the HDR data is related to the spinal cord.

11. The apparatus of claim 1, wherein the processor is further programmed to separate vascular and metabolic contributions to the blood oxygen level dependence using arterial spin labeling ("ASL").

12. A technical system for identifying vascular drainage insufficiency in the central nervous system, the system comprising:
    a non-transitory computer readable medium for storing computer executable programmed modules;
    a processor communicatively coupled with the non-transitory computer readable medium for executing programmed modules stored therein;
    an image acquisition module stored in the non-transitory computer readable medium and configured to be executed by the processor to obtain functional magnetic resonance imaging ("fMRI") data based on blood oxygen level dependence ("BOLD");

a hemodynamic response ("HDR") module stored in the non-transitory computer readable medium and configured to be executed by the processor to convert the fMRI/BOLD data to HDR data, said HDR data comprising a graph of the BOLD over time;

wherein the HDR module is further configured to be executed by the processor to analyze the HDR data and identify a negative trough in the HDR data to determine an abnormal HDR response and identify a vascular drainage insufficiency in the central nervous system based on said abnormal HDR response.

13. The system of claim 12, wherein an abnormal HDR response is identified by the duration of the negative trough in the HDR data.

14. The system of claim 12, wherein an abnormal HDR response is identified by the depth of the negative trough in the HDR data.

15. The system of claim 12, wherein an abnormal HDR response is identified by the area of the negative trough in the HDR data.

16. The system of claim 12, wherein the HDR data is related to the cerebral cortex.

17. The system of claim 12, wherein the HDR data is related to the sub-cortical white matter.

18. The system of claim 12, wherein the HDR data is related to the thalamus.

19. The system of claim 12, wherein the HDR data is related to the basal ganglia.

20. The system of claim 12, wherein the HDR data is related to the brainstem.

21. The system of claim 12, wherein the HDR data is related to the spinal cord.

22. The system of claim 12, wherein the image acquisition module is further configured to be executed by the processor to separate vascular and metabolic contributions to the blood oxygen level dependence using arterial spin labeling ("ASL").

23. A computer implemented method for identifying vascular drainage insufficiency in the central nervous system, comprising:

obtaining, using one or more processors, functional magnetic resonance imaging ("fMRI") data based on blood oxygen level dependence ("BOLD");

converting, using the one or more processors, the fMRI/BOLD data to hemodynamic response ("HDR") data comprising a graph of the BOLD over time;

analyzing, using the one or more processors, the HDR data to determine an abnormal HDR response by identifying a negative trough in the HDR data;

identifying, using the one or more processors, a vascular drainage insufficiency in the central nervous system based on said abnormal HDR response.

24. The method of claim 23, wherein an abnormal HDR response is identified by the duration of the negative trough in the HDR data.

25. The method of claim 23, wherein an abnormal HDR response is identified by the depth of the negative trough in the HDR data.

26. The method of claim 23, wherein an abnormal HDR response is identified by the area of the negative trough in the HDR data.

27. The method of claim 23, wherein the HDR data is related to the cerebral cortex.

28. The method of claim 23, wherein the HDR data is related to the sub-cortical white matter.

29. The method of claim 23, wherein the HDR data is related to the thalamus.

30. The method of claim 23, wherein the HDR data is related to the basal ganglia.

31. The method of claim 23, wherein the HDR data is related to the brainstem.

32. The method of claim 23, wherein the HDR data is related to the spinal cord.

33. The method of claim 23, wherein obtaining functional magnetic resonance imaging data based on blood oxygen level dependence comprises separating vascular and metabolic contributions to the blood oxygen level dependence using arterial spin labeling ("ASL").

34. A non-transitory computer readable medium having stored thereon one or more sequences of instructions for causing one or more processors to perform the steps for identifying vascular drainage insufficiency in the central nervous system, the steps comprising:

obtaining functional magnetic resonance imaging ("fMRI") data based on blood oxygen level dependence ("BOLD");

converting the fMRI/BOLD data to hemodynamic response ("HDR") data comprising a graph of the BOLD over time;

analyzing the HDR data to determine an abnormal HDR response by identifying a negative trough in the HDR data;

identifying a vascular drainage insufficiency in the central nervous system based on said abnormal HDR response.

35. The medium of claim 34, wherein an abnormal HDR response is identified by the duration of the negative trough in the HDR data.

36. The medium of claim 34, wherein an abnormal HDR response is identified by the depth of the negative trough in the HDR data.

37. The medium of claim 34, wherein an abnormal HDR response is identified by the area of the negative trough in the HDR data.

38. The medium of claim 34, wherein the HDR data is related to the cerebral cortex.

39. The medium of claim 34, wherein the HDR data is related to the sub-cortical white matter.

40. The medium of claim 34, wherein the HDR data is related to the thalamus.

41. The medium of claim 34, wherein the HDR data is related to the basal ganglia.

42. The medium of claim 34, wherein the HDR data is related to the brainstem.

43. The medium of claim 34, wherein the HDR data is related to the spinal cord.

44. The medium of claim 34, wherein the step of obtaining functional magnetic resonance imaging data based on blood oxygen level dependence comprises separating vascular and metabolic contributions to the blood oxygen level dependence using arterial spin labeling ("ASL").

* * * * *